United States Patent

Ogata et al.

[11] Patent Number: 5,504,087
[45] Date of Patent: Apr. 2, 1996

[54] 1-PHENOXY-2-PROPANOL DERIVATIVES USEFUL IN TREATING HYPERTENSION AND GLAUCOMA

[75] Inventors: Kazumi Ogata, Toyonaka; Takahiro Sakaue, Itami; Yuuichi Isowaki, Settsu; Takaaki Deguchi, Kobe, all of Japan

[73] Assignee: Senju Pharmaceutical Co., Ltd., Osaka, Japan

[21] Appl. No.: 193,540

[22] Filed: Feb. 8, 1994

[30] Foreign Application Priority Data

Feb. 15, 1993 [JP] Japan .................................... 5-025361
Oct. 14, 1993 [JP] Japan .................................... 5-256739

[51] Int. Cl.⁶ .................... A61K 31/495; C07D 405/06; C07D 295/092; C07C 217/32
[52] U.S. Cl. .................... 514/253; 514/255; 514/652; 544/377; 544/394; 564/349
[58] Field of Search .................... 564/349; 544/377, 544/394; 514/253, 255, 652

[56] References Cited

U.S. PATENT DOCUMENTS

| | | | |
|---|---|---|---|
| 3,211,735 | 10/1965 | de Stevens et al. | 544/394 |
| 3,501,769 | 3/1970 | Crowther et al. | 549/552 |
| 4,760,182 | 7/1988 | Ippolito et al. | 564/349 |

FOREIGN PATENT DOCUMENTS

| | | |
|---|---|---|
| 0089634 | 9/1983 | European Pat. Off. . |
| 0171209 | 2/1986 | European Pat. Off. . |
| 0221788 | 5/1987 | European Pat. Off. . |
| 0498705 | 8/1992 | European Pat. Off. . |
| 1069345 | 5/1967 | United Kingdom . |
| 1123258 | 8/1968 | United Kingdom . |
| 2044251 | 10/1980 | United Kingdom . |

OTHER PUBLICATIONS

Chemical Abstracts, vol. 67, No. 13, 25 Sep. 1967, Columbus, Ohio, US; p. 6011.

*Primary Examiner*—Emily Bernhardt
*Attorney, Agent, or Firm*—Merchant, Gould, Smith, Edell, Welter & Schmidt

[57] ABSTRACT

A hypotensive agent and antiglaucoma agent which comprise a compound represented by the following formula:

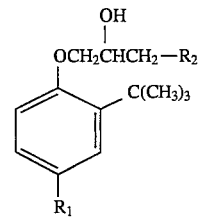

(wherein $R_1$ is hydrogen, or a lower alkyl or lower alkoxy group; $R_2$ is an isopropylamino, tert-butylamino, 2-(2-methoxyphenyl)ethyl-1-amino, 4-(2-methoxyphenyl)]-1-piperazinyl or 4-piperonyl-1-piperazinyl group, provided however that in the case of $R_1$ being hydrogen, $R_2$ is neither isopropylamino nor tert-butylamino group) or its pharmacologically acceptable salt.

6 Claims, 4 Drawing Sheets

1-PHENOXY-2-PROPANOL DERIVATIVES USEFUL IN TREATING HYPERTENSION AND GLAUCOMA

The present invention relates to useful propanolamine derivatives, to a process for producing the same and to their uses. In particular, the present invention relates to 2-propanolamine derivatives or their pharmacologically acceptable salts, to a process for producing the same and to useful hypotensive agents and antiglaucoma agents which contain the same.

It is heretofore known that 2-propanolamine derivatives, with their β-blocking activities or α,β-blocking activities, have been used as a hypotensive agent and antiglaucoma agent.

Nevertheless, these compounds have turned out to be far from being satisfactory in terms of magnitude of such effects. Under these circumstances, the present inventors conducted repeatedly intensive investigation into novel compounds possessing more potent hypotensive and antiglaucoma activities, and as a result, found that such novel compounds as 1-(2-tert-butylphenoxy)-2-propanolamine derivatives, 1-(2-tert-butyl-4-alkoxyphenoxy)-2-propanolamine derivatives and 1-(2-tert-butyl-4-alkylphenoxy)-2-propanolamine derivatives can achieve such objectives. Such a finding, followed by further repeated investigation, culminated into the present invention.

Thus, the present invention relates to (1) compounds represented by the following formula:

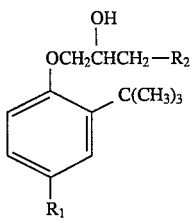

(wherein $R_1$ is hydrogen, or a lower alkyl or lower alkoxy group; $R_2$ is an isopropylamino, tert-butylamino, 2-(2-methoxyphenyl)ethyl-1-amino, 4-(2-methoxyphenyl)-1-piperazinyl or 4-piperonyl-1-piperazinyl group, provided however that in the case of R1 being hydrogen, $R_2$ is neither isopropylamino nor tert-butylamino group, and in the case of $R_1$ being a methyl group, $R_2$ is not an isopropylamino group) or its pharmacologically acceptable salt, to (2) a process for producing the same, to (3) hypotensive agents which contain a compound of the above-described formula or its pharmacologically acceptable salt and to (4) antiglaucoma agents which contain a compound represented by the following formula:

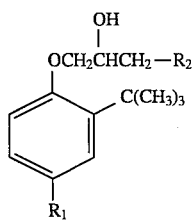

(wherein $R_1$ is hydrogen, or a lower alkyl or lower alkoxy group; $R_2$ is an isopropylamino, tert-butylamino, 2-(2-methoxyphenyl)ethyl-1-amino, 4-( 2-methoxyphenyl )-1-piperazinyl or 4-piperonyl-1-piperazinyl group, provided however that in the case of $R_1$ being hydrogen, $R_2$ is neither isopropylamino nor tert-butylamino group) or its pharmacologically acceptable salt.

Referring to the above-described formula, the lower alkyl group as represented by R1 preferably is a straight-chain or cyclic alkyl group having a number of carbon atoms of 1 to 5, and there may be mentioned for example methyl, ethyl, n-propyl, isopropyl, cyclopropyl, n-butyl, tert-butyl, sec-butyl, n-pentyl, 1-ethylpropyl and isopentyl groups.

With reference to the above-described formula, the lower alkoxy group as represented by R1 preferably is an alkoxy group having a number of carbon atoms of 1 to 5, and is exemplified by methoxy, ethoxy, propoxy, isopropoxy, n-butoxy, iso-butoxy, tert-butoxy, n-pentyloxy, neopentyloxy, 2-methylbutoxy, 1,2-dimethylpropoxy and 1-ethylpropoxy groups.

The compounds represented by the above-described formula, in the form of either a free compound or pharmacologically acceptable salt, can suitably be used for the purpose of this invention. Examples of such a salt include inorganic salts, such as hydrochloride and sulfate, and organic salts, such as maleate and tartrate, and any acid salts other than those can suitably be utilized, as long as if they are pharmacologically acceptable.

The compounds of the present invention and the compounds that are contained in the pharmaceutical preparations of the present invention (collectively referred to as "the present compounds") can be synthesized for example through the following pathway of synthesis or any other pathways in accordance with the same.

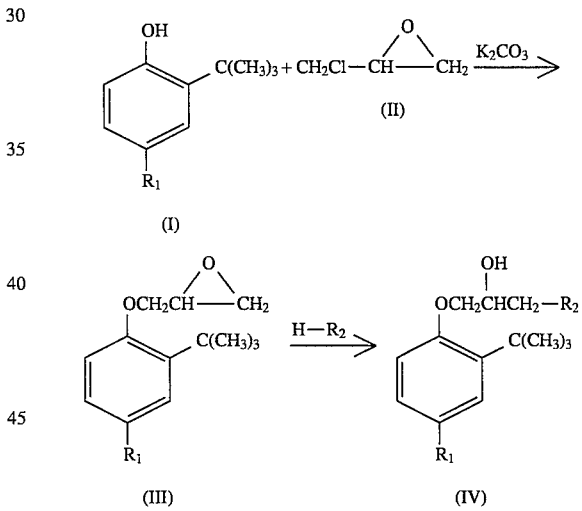

In the above formulae, R1 represents hydrogen or a lower alkyl or lower alkoxy group, and R2 designates an isopropylamino, tert-butylamino, 2-(2-methoxyphenyl)ethyl-1-amino, 4-(2-methoxyphenyl)]-1-piperazinyl or 4-piperonyl-1-piperazinyl group.

Thus, 2-tert-butyl-4-alkoxyphenol, 2-tert-butylphenol or 2-tert-butyl-4-alkylphenol and epichlorohydrin (II) are refluxed in a solvent such as methyl ethyl ketone and acetone, in the presence of an alkali such as alkali hydroxide or carbonate (e.g., anhydrous potassium carbonate) for about 4 to 12 hours to give the individually corresponding 1-(2, 3-epoxypropoxy)-2-tert-butyl-4-alkoxybenzene, 2-tert-butyl-1-(2,3-epoxypropoxy)benzene or 1-(2,3-epoxypropoxy)-2-tert-butyl-4-alkylbenzene (III). As a solvent being usable in this reaction step, any solvents other than the above-mentioned ones may be utilized unless they inhibit the reaction. Subsequently, the compound (III) is allowed to undergo addition with amines, H-R2 [tertbutylamine, isopropyl-amine, 1-(2-methoxyphenyl)piperazine, 2(2-methoxyphenyl)-ethyl-1-amine, 1-piperonylpiperazine] by refluxing in methanol for about 4 to 12 hours to produce the individually corresponding 1-(2-tert-butyl-4-alkoxyphenoxy)-2-propanolamine derivatives, 1-(2-tert-butylphenoxy)-2-propanolamine derivatives or 1-(2-tert-butyl-4-alkylphenoxy)-2-propanolamine derivatives (IV). As a solvent being employable in this reaction step, any solvents other than the above-mentioned one may be used unless they inhibit the reaction. The present compounds (IV) as obtained by the above-described procedure can be purified by recrystallization from an appropriate solvent, such as water, alcohol-based solvents, solvent mixtures thereof or water-miscible solvent mixtures (e.g., acetone, tetrahydrofuran, etc.). If necessary, furthermore, the present compounds are treated with inorganic acids, such as hydrochloric acid and sulfuric acid, and organic acids, such as maleic acid and tartaric acid, to give the respectively corresponding acid salts.

The present compounds (IV) as produced by the above procedure are the novel compounds being not described in literature and are useful as a hypotensive agent and antiglaucoma agent. It is to be added that the compounds of the above formula (IV) (refer to Reference Example 1 to be described below) wherein $R_1$ is hydrogen, with $R_2$ being isopropylamino or tert-butylamino group, and wherein R1 is methyl group, with R2 being isopropylamino group, are known compounds already described in literature. Among such known compounds, the compound of the formula (IV) wherein R1 is hydrogen and R2 is isopropyl amino or tert-butylamino group was observed to exhibit little intraocular-pressure reducing activity (antiglaucoma activity), unlike the present compounds.

The medicinal preparations of the present invention can be provided with one or a suitable combination of not less than two of the present compounds, depending upon the purpose and necessity or requirements.

The medicinal preparations of the present invention are suitably used orally or parenterally as a hypotensive agent and antiglaucoma agent. Referring to the dosage form, they can be processed into any forms, such as solid dosage forms being exemplified by tablets, granules, powders and capsules, and liquid dosage forms being exemplified by injectable solutions and ophthalmic solutions, by the known procedures. These dosage forms may be formulated with a variety of conventionally employed additives, such as excipients, binders, thickening agents, dispersing agents, reabsorption accelerating agents, buffers, surfactants, dissolving auxiliary agents, preservatives, emulsifiers, isotonizing agents, stabilizers and pH adjusting agents.

The present compounds in the objective of this invention are dosed at varied rates depending upon the kind of the present compounds to be used, the body weight and age of a patient, and the type and conditions of a disease, and are desirably administered adult patients at a single dose in the range of about 1 to 10 mg per day, when processed into an injectable solution, and, in the case of oral tablets, at a single dose in the region of about 1 to 100 mg several times a day. In cases where the present compounds are processed into ophthalmic solutions, it is advisable to give such ophthalmic solutions prepared at concentrations of about 0.05 to 5 (W/V) % topically to the eyes of an adult patient at a single dose of several drops several times a day.

The medicinal preparation of the present invention may suitably be incorporated with other ingredients of hypotensive and antiglaucoma agents and/or different types of active ingredients, unless contrary to the objective of the present invention.

Below described are the examples to illustrate the present invention in detail:

EXAMPLE 1

1-(2-tert-Butyl-4-methoxyphenoxy)-3-tert-butylamino-2-propanol hydrochloride [$R_1$=OCH$_3$; $R_2$=-NHC(CH$_3$)$_3$]

In 150 ml of methyl ethyl ketone were dissolved 4.5 g (0.025 mole) of 4-hydroxy-3-tert-butylanisole and 8 g of epichlorohydrin, and 7.0 g of potassium carbonate is added to the resultant solution, followed by heating under reflux for 8 hours. The precipitated inorganic salt is filtered out, and the filtrate is concentrated. The oily-formed residue is extracted with ethyl acetate, and the extract is washed successively with 1% aqueous sodium hydroxide and water, and the ethyl acetate is distilled off to give about 5 g of 4-(2,3-epoxypropoxy)-3-tert-butylanisole in the form of oily substance. The oily substance and 4.6 g of tert-butylamine are dissolved in 100 ml of methanol, followed by heating under reflux for 10 hours, and the solvent is distilled off. The oily residue is admixed with 200 ml of water, and the mixture is made acid with hydrochloric acid, stirred and extracted with isopropyl ether to remove the unreacted materials. The resulting aqueous solution is concentrated under reduced pressure, and the white crystals that crystallize out are recovered by filtration. Recrystallization from water gives 1.3 g of the objective compound, m.p. of 177° to 179° C.

Elementary analysis, for $C_{18}H_{31}O_3N \cdot HCl$

Calcd.(%): C, 62.50; H, 9.32; N, 4.05

Found (%): C, 62.47; H, 9.42; N, 4.02

Figure 1:
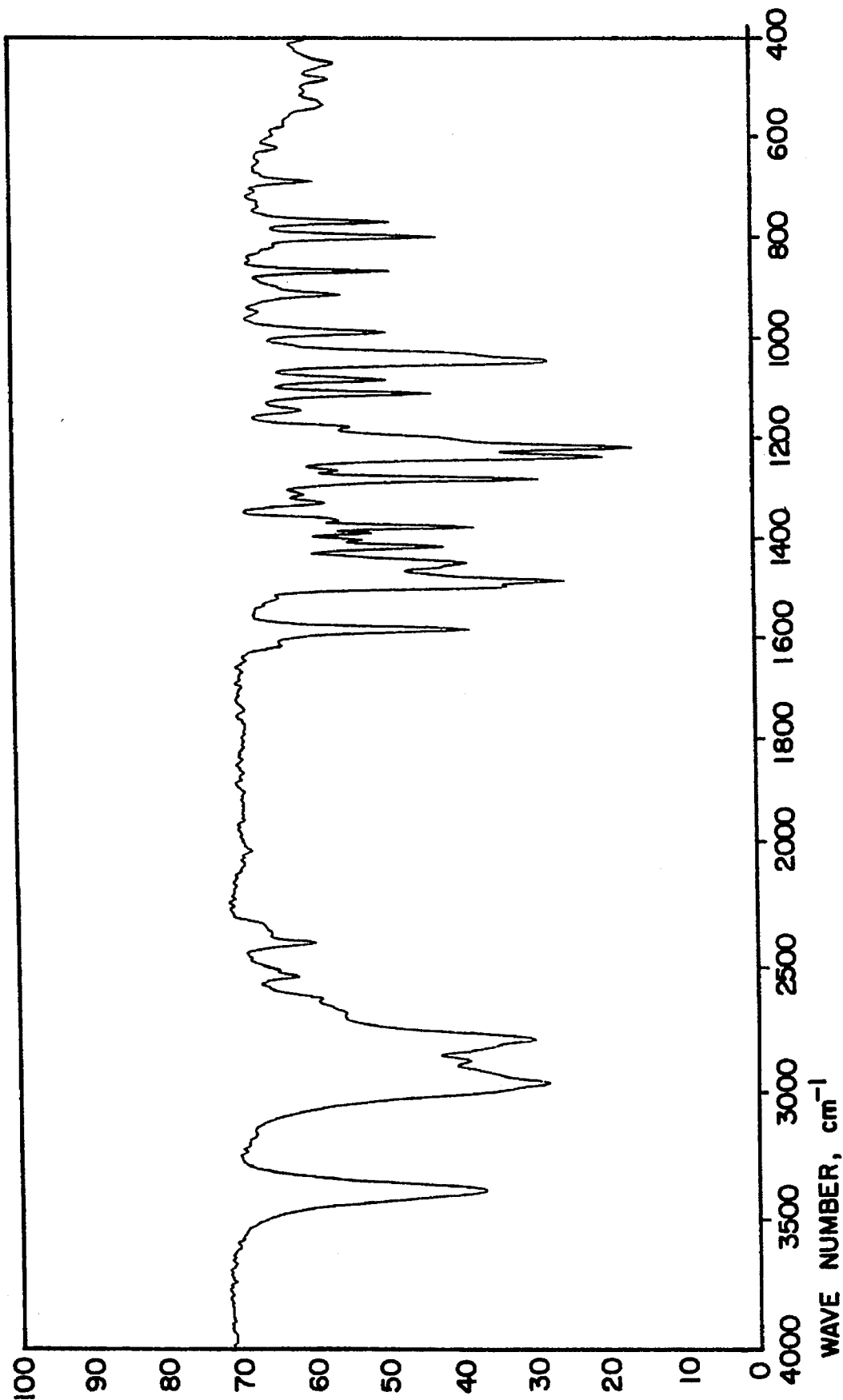
FIGS. 1 through 4 illustrate the infra-red absorption spectrum for examples 1, 3, 7 and reference example 1, respectively.

Shown in FIG. 1 is an infra-red absorption spectrum (IR) of the compound as synthesized in Example 1.

EXAMPLE 2

1-(2-tert-Butyl-4-methoxyphenoxy)-3-isopropylamino-2-propanol hydrochloride [$R_1$=OCH$_3$, $R_2$=—NHCH(CH$_3$)$_2$]

By following the procedure as described in Example 1, 4.5 g of 4-hydroxy-3-tert-butylanisole is treated to give 4-(2,3-epoxypropoxy)-3-tert-butylanisole, which is then reacted with 5 g of isopropylamine and 100 ml of methanol being added in the same manner as described in Example 1 to produce white crystals. Recrystallization from ethanol-isopropyl ether yields 1.0 g of the objective compound, m.p. of 120° to 121° C.

Elementary analysis, for $C_{17}H_{29}O_3N \cdot HCl$

Calcd.(%): C, 61.52; H, 9.11; N, 4.22

Found (%): C, 61.33; H, 9.21; N, 4.20

EXAMPLE 3

1-(2-tert-Butyl-4-methoxyphenoxy)-3-[4-(2-methoxyphenyl)-1-piperazinyl]-2-propanol hydrochloride [$R_1$=OCH$_3$, $R_2$=—NC$_4$HN$_8$—C$_6$H$_4$OCH$_3$]

By following the procedure as described in Example 1, 4.5 g of 4-hydroxy-3-tert-butylanisole is treated to give 4-(2,3-epoxypropoxy)-3-tert-butylanisole, which is then heated for 10 hours with 4.8 g of 1-(2-methoxyphenyl)piperazine and 100 ml of methanol being added. The methanol is distilled off, and the residue is treated with 40 ml of 2N-HCl and 30 ml of isopropyl ether being added. The white crystals that crystallize out are recovered by filtration and recrystallized from methanol-ethanol to give 2.3 g of the objective compound, m.p. of 206° to 208° C.

Elementary analysis, for $C_{25}H_{36}O_4N_2 \cdot 2HCl$
Calcd.(%): C, 59.88; H, 7.64; N, 5.59
Found (%): C, 59.66; H, 7.53; N, 5.60

Figure 2:
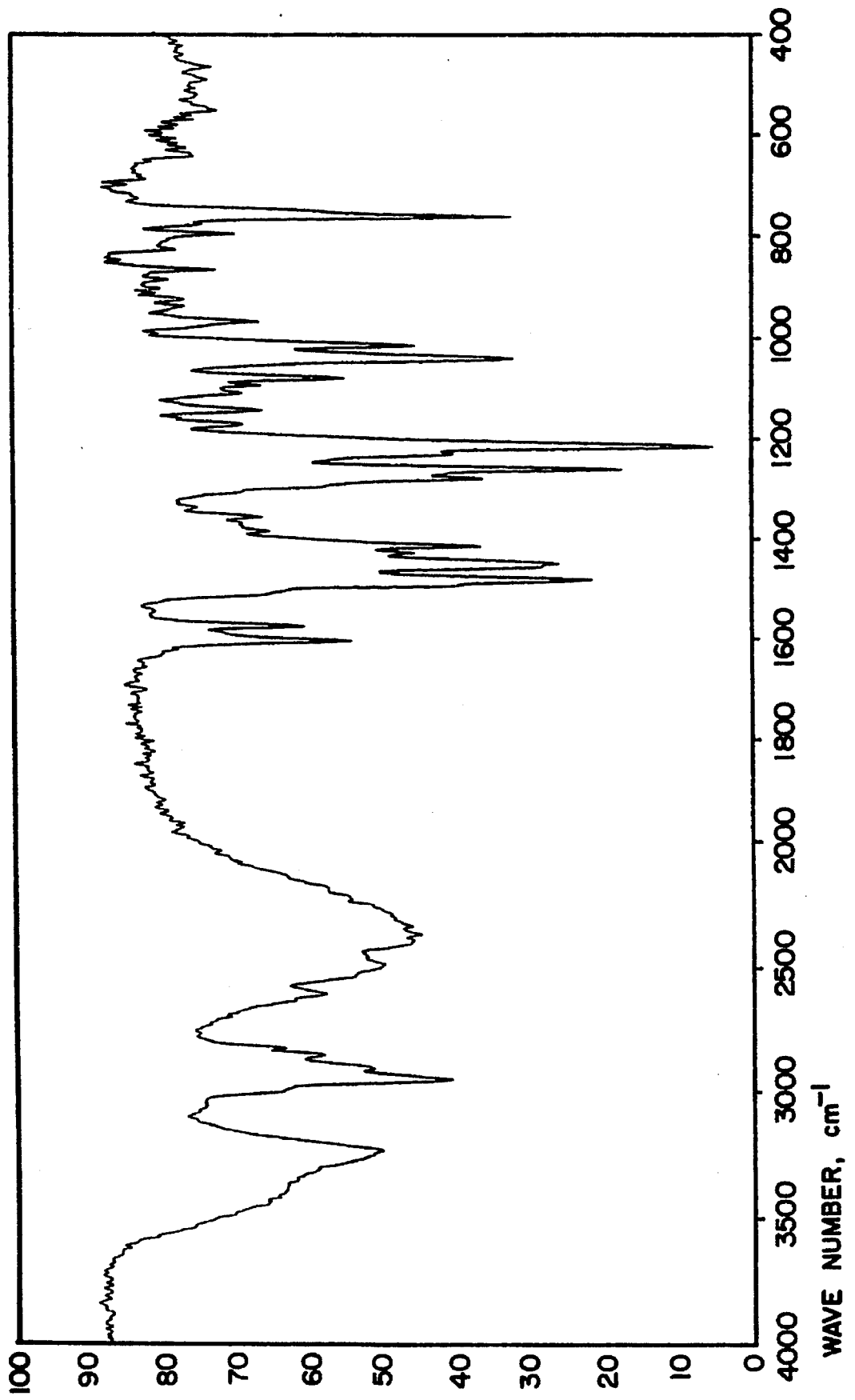

Shown in FIG. 2 is an infra-red absorption spectrum (IR) of the compound as synthesized in Example 3.

EXAMPLE 4

1-(2-tert-Butyl-4-methoxyphenoxy)-3-[2-(2-methoxyphenyl)-ethyl-1-amino]-2-propanol hydrochloride [$R_1$=OCH$_3$, $R_2$= —NHCH$_2$CH$_2$C$_6$H$_4$OCH$_3$]

By following the procedure as described in Example 1, 4.5 g of 4-hydroxy-3-tert-butylanisole is treated to give 4-(2,3-epoxypropoxy)-3-tert-butylanisole, which is then reacted with 3.8 g of 2-(2-methoxyphenyl)ethyl-1-amine as dissolved in 100 ml of methanol. The treatment is conducted in the same manner as described in Example 3 to give crystals. The crystals are recovered by filtration and recrystallized from methanol-ethanol to give 2.2 g of the objective compound, m.p. of 159° to 161° C.

Elementary analysis, for $C_{23}H_{33}O_4N \cdot HCl$
Calcd.(%): C, 65.16; H, 8.08; N, 3.30
Found (%): C, 65.20; H, 8.00; N, 3.23

EXAMPLE 5

1-(2-tert-Butyl-4-methoxyphenoxy)-3-(4-piperonyl-1-piperazinyl]-2-propanol hydrochloride [$R_1$=OCH$_3$, $R_2$= —NC$_4$H$_8$N—CH$_2$—C$_6$H$_3$O$_2$CH$_2$]

By following the procedure as described in Example 3, 4.5 g of 4-hydroxy-3-tert-butylanisole and 5.6 g of 1-(piperonyl)piperazine are subjected to the reaction to give crystals. The crystals are recovered by filtration and recrystallized from ethanol to give 2.5 g of the objective compound, m.p. of 218° to 220° C.

Elementary analysis, for $C_{26}H_{36}O_5N_2 \cdot 2HCl(^1/_2)H_2O$
Calcd.(%): C, 57.99; H, 7.30; N, 5.20
Found (%): C, 57.97; H, 7.19; N, 5.39

EXAMPLE 6

1-(2-tert-Butylphenoxy)-3-[4-(2-methoxyphenyl)-1-piperazinyl]-2-propanol hydrochloride [$R_1$=H, $R_2$=—NC$_4$H$_8$N—C$_6$H$_4$OCH$_3$]

By following the procedure as described in Example 1, 3.75 g of 2-tert-butylphenol, 8 g of epichlorohydrin, 7.0 g of anhydrous potassium Carbonate and 150 ml of methyl ethyl ketone are allowed to undergo the reaction, followed by reaction with 4.8 g of 1-(2-methoxyphenyl)piperazine in the same manner as described in Example 3. The reaction mixture is admixed with 130 ml of 2N—HCl and 30 ml of methanol and left on standing to precipitate white crystals. The crystals are recovered by filtration and recrystallized from methanol-water to give 2.5 g of the objective compound, m.p. of 153° to 155° C.

Elementary analysis, for $C_{24}H_{34}O_3N_2 \cdot 2HCl$
Calcd.(%): C, 61.14; H, 7.70; N, 5.94
Found (%): C, 61.08; H, 7.67; N, 5.88

EXAMPLE 7

1-(2-tert-Butyl-4-methylphenoxy)-3-[4-(2-methoxyphenyl)-1-piperazinyl]-2-propanol hydrochloride [$R_1$=CH$_3$, $R_2$= —NC$_4$H$_8$N—C$_6$H$_4$OCH$_3$]

By following the procedure as described in Example 1, 4.1 g of 2-tert-butyl-4-cresol is treated to give about 5 g of 4-(2,3-epoxypropoxy)-3-tert-butyltoluene, which is then heated under reflux for 10 hours with 4.8 g of 1-(2-methoxyphenyl)piperazine and 100 ml of methanol being added. After the solvent is distilled off, the residue is dissolved in 200 ml of ethanol and the solution is made acid with hydrochloric acid under ice-cooling. The white crystals that crystallize out are recovered by filtration and recrystallized from water-ethanol to give 5.51 g of the objective compound, m.p. of 188° to 190° C.

Elementary analysis, for $C_{25}H_{36}N_2O_3 \cdot 2HCl$
Calcd.(%): C, 61.85; H, 7.89; N, 5.77
Found (%): C, 61.63; H, 7.79; N, 5.66

Figure 3:
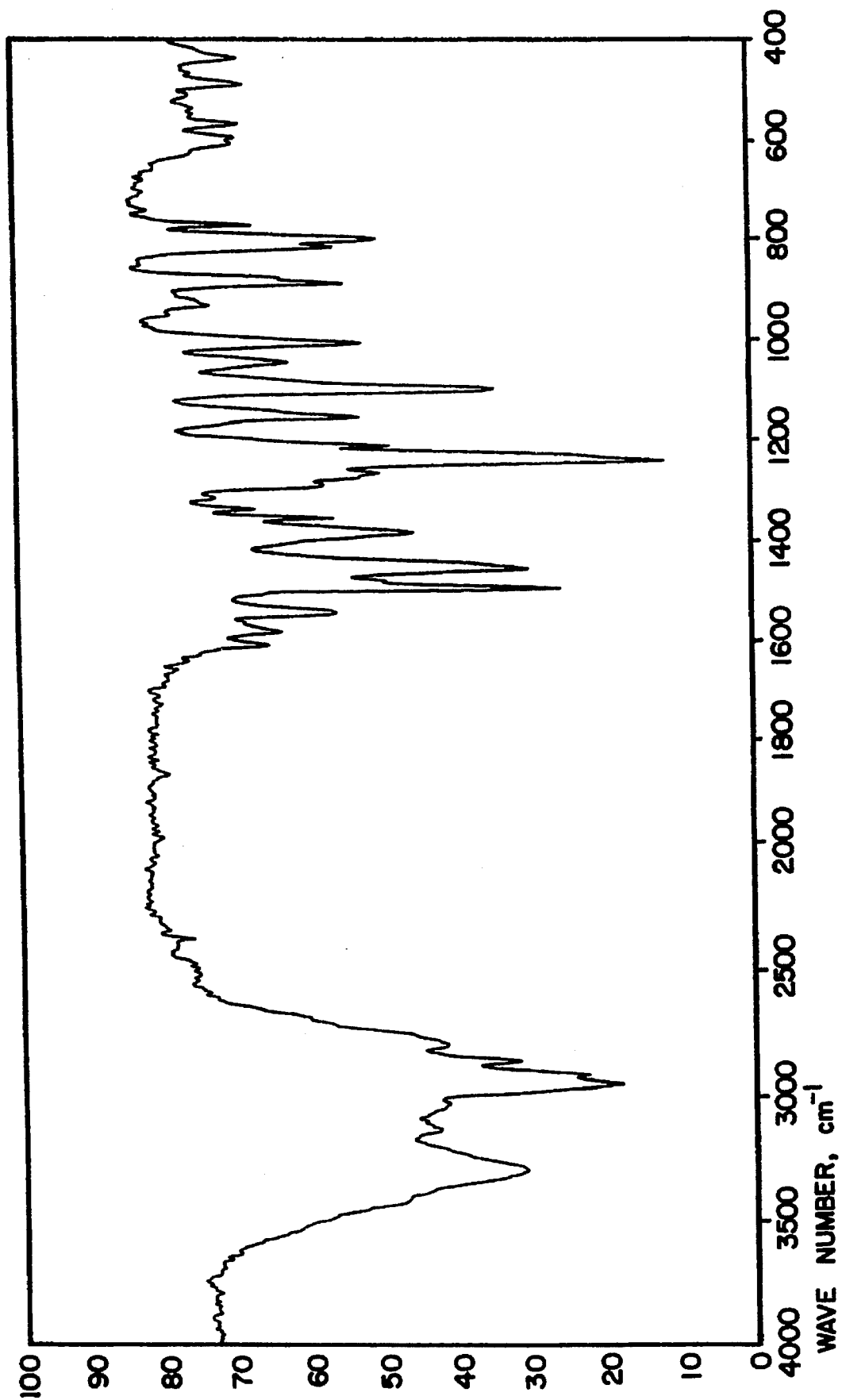

Shown in FIG. 3 is an infra-red absorption spectrum (IR) of the compound as synthesized in Example 7.

Reference Example 1 (known compound):

1-(2-tert-Butyl-4-methylphenoxy)-3-isopropylamino-2-propanol hydrochloride [$R_1$ =CH$_3$, $R_2$=—NHCH(CH$_3$)$_2$]

By following the procedure as described in Example 1, 4.1 g of 2-tert-4-cresol is treated to give 4-(2,3-epoxypropoxy)-3-tert-butyltoluene, which is then heated under reflux for 10 hours with 5.1 g of isopropylamine and 100 ml of methanol being added. After the solvent is distilled off, the residue is treated with 200 ml of ethanol added and the mixture is made acid with hydrochloric acid, under ice-cooling, followed by stirring. The mixture is admixed with ethyl ether, and the white crystals that crystallize out are recovered by filtration and recrystallized from ethanol-ethyl ether to give 2.4 g of the objective compound, m.p. of 159° to 161° C.

Elementary analysis, for $C_{17}H_{29}NO_2 \cdot HCl$
Calcd.(%): C, 64.64; H, 9.57; N, 4.43
Found (%): C, 64.45; H, 9.43; N, 4.46

Figure 4:
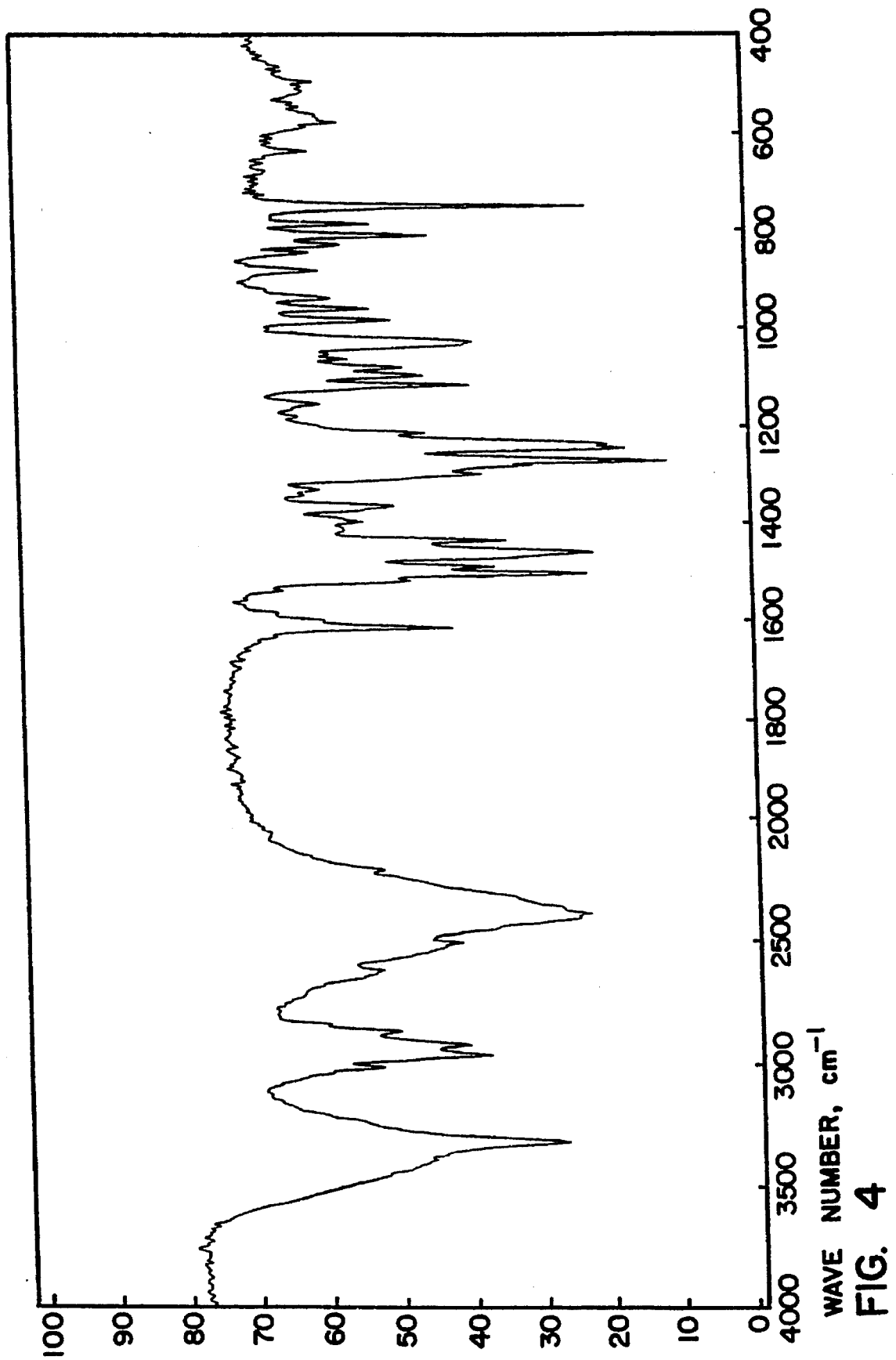

Shown in FIG. 4 is an infra-red absorption spectrum (IR) of the compound as synthesized in Reference Example 1.

EXAMPLE 8

Intraocular-pressure reducing activity of the present compounds

The present compounds were tested for their intraocular-pressure reducing activity.

[Test method]

The present compound as a test drug substance, after being dissolved in 5% aqueous dimethylsulfoxide (DMSO) solution to a test solution of a specified concentration having its pH adjusted to about 6 with 1N—NaOH, was applied topically in 50 µl portion to one eye of a colored rabbit having ordinary intraocular pressure, while isotonic saline containing a 5% aqueous DMSO solution as a control was instilled in the same portion to the other, and the intraocular pressures (mmHg) in both eyes were measured before the treatment and 0.5, 1, 2 and 4 hours after the treatment, respectively.

[Test results]

| Com-pound (No. of Ex.) | Concn. % | Eye | Intraocular pressure measurement, mmHg | | | | |
|---|---|---|---|---|---|---|---|
| | | | Before | 0.5 hr | 1 hr | 2 hr | 4 hr |
| 1 | 0.5 | Treated | 23.33 | 21.50 | 22.00 | 21.67 | 22.83 |
| | | Control | 22.67 | 22.33 | 22.33 | 22.67 | 23.83 |
| 3 | 0.1 | Treated | 24.00 | 21.00 | 20.83 | 22.33 | 24.33 |
| | | Control | 23.50 | 23.67 | 23.50 | 24.00 | 24.00 |
| 4 | 0.1 | Treated | 23.00 | 19.83 | 21.17 | 22.00 | 22.33 |
| | | Control | 23.00 | 23.17 | 22.83 | 22.67 | 23.0 |
| 5 | 0.1 | Treated | 23.17 | 21.00 | 21.67 | 22.33 | 23.00 |
| | | Control | 23.50 | 23.00 | 23.33 | 23.33 | 24.00 |
| 6 | 0.1 | Treated | 24.00 | 21.67 | 22.50 | 24.00 | 24.00 |
| | | Control | 24.00 | 23.83 | 23.17 | 24.00 | 24.33 |
| Compound of Ref. Ex. 1 | 0.5 | Treated | 23.58 | 20.25 | 19.67 | 19.75 | 22.08 |
| | | Control | 23.25 | 23.25 | 23.33 | 23.08 | 24.00 |

Note: Each figures indicate a mean value of intraocular pressure measurements taken for 3 eyes, except the compound of Reference Example 1 where each figure designates a mean value of intraocular pressure measurements taken for 6 eyes.

The present compounds reduced intraocular pressure by about 2 to 4 mmHg up to 1 hour after instillation, and turned out to be useful as an antiglaucoma agent. The compounds of the present invention did not affect the pupil's diameter.

EXAMPLE 9

Hypotensive activities of the present compounds

The present compounds were tested for their hypotensive activities.

[Test method]

Spontaneous hypertension rats (SHR) weighing about 270 g, as purchased from K. K. Hoshino Animal Breeding Co., were used as a test animal, being divided into groups each consisting of 5 heads.

The test substance, as suspended in 0.5% aqueous sodium carboxymethylcellulose (CMC-Na) solution was given rats orally at a dose of 30 mg/kg body weight, and blood pressure was measured indirectly by means of the Tail-cuff method before administration as well as 0.5, 1, 1.5 and 2 hours after the same (Indirect automatic blood-pressure measuring apparatus BP-98, manufactured by K. K. Softron), while rats were warmed at 38° C. for 10 min with rat's pulse rate being kept at 350 to 500. The results are shown in Table 2.

TABLE 2

[Test Results] Blood pressure measurements

| Compound (No. of Example) | Blood pressure measurement, mmHg | | | | |
|---|---|---|---|---|---|
| | 0 | 0.5 | 1 | 1.5 | 2 hr |
| 0.5% CMC-Na (control) | 184.7 | 178.2 | 172.7 | 172.6 | 173.3 |
| 1 | 167.1 | 160.0 | 149.9 | 143.5 | 132.8 |

TABLE 2-continued

[Test Results] Blood pressure measurements

| Compound (No. of Example) | Blood pressure measurement, mmHg | | | | |
|---|---|---|---|---|---|
| | 0 | 0.5 | 1 | 1.5 | 2 hr |
| 3 | 171.9 | 163.3 | 154.1 | 151.1 | 155.6 |

Note: Each figure indicates a mean value of measurements taken for 5 animals.

As is shown in Table 2, the compounds of the present invention reduced blood pressure in spontaneous hypertension rats by 20 to 35 mmHg and were found to be useful as a hypotensive agent.

EXAMPLE 10

Tablets for internal use

| | |
|---|---|
| 1-(2-tert-Butyl-4-methoxyphenoxy)-3-[4-(2-methoxyphenyl)-1-piperazinyl]-2-propanol hydrochloride | 30 mg |
| Lactose | 80 mg |
| Starch | 17 mg |
| Polyethylene glycol 6000 | 3 mg |

The above-described ingredients as a starting material for the production of one tablet are compressed into a tablet by the conventional procedure.

EXAMPLE 11

Ophthalmic solution

| | |
|---|---|
| 1-(2-tert-Butyl-4-methoxyphenoxy)-3-tert-butylamino-2-propanol hydrochloride | 0.5 g |
| Sodium chloride | 0.6 g |
| Boric acid | 0.7 g |
| Benzalkonium chloride | 0.005 g |
| Sodium hydroxide | Appropriate |
| Sterilized purified water | To make the total to 100 ml |
| Total | 100 ml, with pH 6.5 |

The above ingredients are mixed, and the solution is sterile filtered to produce an ophthalmic solution.

We claim:

1. The compound 1-(2-t-butyl-4-methoxyphenoxy)-3-(4-piperonyl-1-piperazinyl)-2-propanol or a pharmaceutically acceptable salt thereof.

2. The compound of claim 1, in the form of the hydrochloride salt.

3. An antiglaucoma agent which comprises an amount effective for treating glaucoma of the compound 1-(2-t-butyl-4-methoxyphenoxy)-3-(4-piperonyl-1-piperazinyl)-2-propanol or a pharmaceutically acceptable salt thereof, and a pharmaceutically acceptable carrier.

4. The antiglaucoma agent of claim 3, wherein the active compound is in the form of the hydrochloride salt.

5. The antiglaucoma agent of claim 3, wherein the carrier is in the form of an ophthalmic solution.

6. The antiglaucoma agent of claim 5, wherein the active compound is present in an amount from about 0.05 to 5% (W/V).

* * * * *